United States Patent [19]
Berntsson et al.

[11] 3,996,382
[45] Dec. 7, 1976

[54] PHENOXY-HYDROXYPROPYLAMINES, THEIR PREPARATION, AND METHOD AND PHARMACEUTICAL PREPARATIONS FOR TREATING CARDIOVASCULAR DISEASES

[75] Inventors: Peder Bernhard Berntsson, Vastra Frolunda; Arne Elof Brändström, Goteborg; Enar Ingemar Carlsson, Kungsbacka; Stig Åke Ingemar Carlsson, Molnlycke; Lars Ek, Onsala; Benny Roger Samuelsson, Pixbo; Sven Erik Sjastrand, Kungsbacka; Gert Christer Strandlund, Molndal; Bengt Arne Hjalmar Ablad, Goteborg, all of Sweden

[73] Assignee: Aktiebolaget Hassle, Goteborg, Sweden

[22] Filed: Apr. 4, 1973

[21] Appl. No.: 347,625

[30] Foreign Application Priority Data
Apr. 4, 1972 Sweden .............. 4321/72

[52] U.S. Cl. .............. 424/330; 260/570.7
[51] Int. Cl.² .............. A61K 31/135; C07C 93/06
[58] Field of Search .............. 424/330; 260/570.7

[56] References Cited
UNITED STATES PATENTS

| | | | |
|---|---|---|---|
| 3,203,992 | 8/1965 | Kunz et al. | 424/330 |
| 3,275,654 | 9/1966 | Wilhelm et al. | 424/330 |
| 3,542,872 | 11/1970 | Koppe et al. | 424/330 |
| 3,542,874 | 11/1970 | Keizer et al. | 424/330 |
| 3,632,780 | 1/1972 | Keizer et al. | 424/330 |
| 3,639,634 | 2/1972 | Marshall | 424/330 |
| 3,644,469 | 2/1972 | Koppe et al. | 424/330 |
| 3,663,607 | 5/1972 | Barrett et al. | 424/330 |
| 3,674,840 | 7/1972 | Grandstrom | 424/330 |
| 3,740,443 | 6/1973 | Koppe et al. | 424/330 |
| 3,740,444 | 6/1973 | Koppe et al. | 424/330 |
| 3,876,802 | 4/1975 | Brandstrom et al. | 424/330 |

OTHER PUBLICATIONS

Dawes et al., Brit. J. Pharmacol. (1950), 5, pp. 65–76.
Burger, "Medicinal Chemistry" 2nd Ed. (1960) Interscience Publishers, Inc. N.Y. p. 43.

*Primary Examiner*—Donald B. Moyer
*Attorney, Agent, or Firm*—Brumbaugh, Graves, Donohue & Raymond

[57] ABSTRACT

Ortho-para-substituted phenoxy-hydroxypropylamines having the general formula

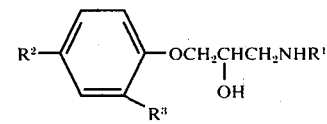

and pharmaceutically acceptable, non-toxic acid addition salts thereof, wherein $R^1$ is alkyl or hydroxy alkyl, $R^2$ is alkoxyalkyl, alkylthioalkyl, alkoxycarbonylaminoalkyl, or alkoxyalkoxy, and $R^3$ is halogen, alkyl, alkenyl, alkinyl, alkoxymethyl, or alkoxy are disclosed as are methods for their preparations;

Pharmaceutical preparations are prepared whose active ingredients include at least one of the newly discovered phenoxy-hydroxypropylamine compounds. Therapeutically effective doses of these preparations selectively block the β-receptors of the heart making them useful in treating heart diseases in animals including humans.

12 Claims, No Drawings

PHENOXY-HYDROXYPROPYLAMINES, THEIR PREPARATION, AND METHOD AND PHARMACEUTICAL PREPARATIONS FOR TREATING CARDIOVASCULAR DISEASES

The present invention relates to new amines of formula I

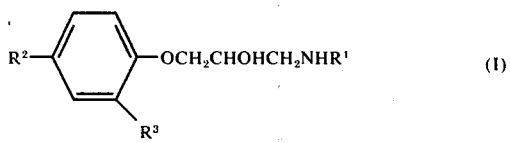

wherein $R^1$ is alkyl or hydroxy alkyl, $R^2$ is alkoxyalkyl, alkoxyalkoxy alkylthioalkyl, or alkoxycarbonylaminoalkyl and $R^3$ is halogen, alkyl, alkenyl, alkinyl, alkoxymethyl or alkoxy and a process for their preparation.

Above and below the terms alkyl, alkenyl and alkinyl residue will be understood to be such as those having up to 7 carbon atoms, preferably up to 4 carbon atoms. Thus, when $R^1$ is alkyl, it has suitably up to 7 carbon atoms and preferably up to 4 carbon atoms. It may be straight or branched, especially branched at the alpha carbon atom. Examples are sec-butyl or tert.-butyl or isopropyl.

When $R^1$ is hydroxyalkyl, it has up to 7 carbon atoms, preferably up to 4 carbon atoms. It may be straight or branched, especially branched at the alpha carbon atom. Examples are 1-hydroxypropyl-2 or 1-hydroxy-2-methyl-propyl-2.

When $R^2$ is alkoxyalkyl, it has in its lower alkoxy part up to 7 carbon atoms, preferably up to 4 carbon atoms, such as iso- or n-propyl and straight or branched butyl, pentyl, hexyl or heptyl. Ethyl and methyl are particularly preferred.

The alkyl part carrying the alkoxy part of group $R^2$ has up to 7 carbon atoms, preferably up to 4 carbon atoms, and is branched or a straight alkylene having especially 2 to 4 carbon atoms in the alkylene chain as ethylene-1,2, butylene-1,4 or preferably propylene-1,3. Examples of suitable alkoxy alkyl radicals are methoxymethyl 1,2-methoxyethyl, 2-ethoxyethyl, 3-ethoxy-n-propyl, 4-methoxy-n-butyl, and especially 3-methoxy-n-propyl.

When $R^2$ is alkoxyalkoxy, the alkyl part in the end position corresponds to the alkyl part of alkoxyalkyl $R^2$ and the alkyl part between the two oxygen atoms corresponds to the alkoxy carrying alkyl part of alkoxyalkyl $R^2$. Examples are methoxymethoxy, ethoxymethoxy, 2-methoxyethoxy, 1-methoxyethoxy, 4-methoxy-n-butoxy, 3-methoxy-n-butoxy. 3-Methoxy-n-propoxy is preferred.

When $R^2$ is alkylthioalkyl, the hydrocarbon part of the alkylthio part and the alkyl part carrying the alkylthio part are analogous to the alkoxyalkyl $R^2$. Examples are methylthiomethyl, 2-methylthioethyl, 2-ethylthioethyl, 3-ethylthio-n-propyl, 4-methylthio-n-butyl, and preferably 3-methylthio-n-propyl.

When $R^2$ is alkoxycarbonylaminoalkyl, the hydrocarbon part of the alkoxy part has the meaning given for the alkyloxy part of the alkoxyalkyl $R^2$ and the alkyl part which carries the alkoxycarbonylamino part corresponds to the alkyl carrying lower alkoxy part of alkoxyalkyl $R^2$. Examples are methoxycarbonylaminomethyl, ethoxycarbonylaminomethyl, 4-methoxycarbonylamino-n-butyl, 2-ethoxycarbonylaminoethyl, 3-ethoxycarbonylamino-n-propyl, 2-methoxycarbonylaminoethyl, and 3-methoxycarbonylamino-n-propyl are preferred.

Examples of $R^3$ when halogen are fluoro, bromo and preferably chloro. When $R^3$ is alkyl, it has up to 7 carbon atoms, preferably up to 4 carbon atoms. Examples are iso- and n-propyl, straight or branched chain butyl, pentyl, hexyl, and heptyl. Ethyl and methyl are preferred.

When $R^3$ is alkenyl it has up to 7 carbon atoms, preferably 2 to 4 carbon atoms. Examples are, 2-methylvinyl, methallyl, and preferably allyl.

When $R^3$ is alkinyl, it has up to 7 carbon atoms, preferably 2 to 4 carbon atoms. Examples are 1-propinyl, 2-propinyl and ethinyl.

When $R^3$ is alkoxymethyl its alkoxy part has up to 7 carbon atoms. Preferably up to 4 carbon atoms. Examples are ethyl, iso- or n-propyl, and methyl. Ethoxymethyl and methoxymethyl are preferred.

When $R^3$ is alkoxy it has up to 7 carbon atoms, preferably up to 4 carbon atoms. Examples are ethoxy, iso- or n-propoxy, and preferably methoxy.

The new compounds have valuable pharmacological properties. Thus, they block cardial $\beta$-receptors, which is shown at the determination of the antagonism of tachycardia after an intravenous injection of 0.5 $\mu$g/kg of d/l-isoproterenol sulphate on an anaesthetized cat at an intravenous dose of 0.002 to 2 mg/kg. Further, they block the vascular $\beta$-receptors, which is shown at the determination of the antagonism of vasodilation after an intravenous injection of 0.5 $\mu$g/kg of d/l-isoproterenol sulphate on an anaesthetized cat at an intravenous dose of 3 mg/kg or more. Furthermore, they block the cardial $\beta$-receptors, which is shown at the determination of tachycardia after the addition of 0.005 $\mu$g/ml of d/l-isoproterenol sulphate to a bath containing an isolated guinea-pig heart in vitro at a concentration of 0.02 to 2 mg/ml.

The new compounds can be used as cardioselective antagonists of adrenergic $\beta$-receptor-stimulators e.g. at the treatment of arrhythmias and angina pectoris. One may also use them as valuable intermediates at the preparation of other useful compounds, especially pharmaceutically active compounds.

One preferred group of amines are those according to formula Ia

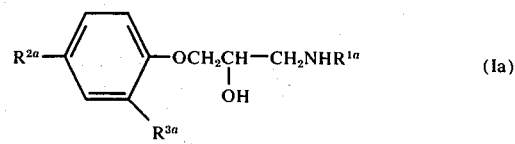

wherein $R^{1a}$ is alkyl having 1 to 4 carbon atoms or hydroxyalkyl having 1 to 4 carbon atoms, $R^{2a}$ is alkoxyalkyl or alkoxyalkoxy having up to 8 carbon atoms and $R^{3a}$ is halogen, alkyl having 1 to 4 carbon atoms, alkenyl having 2 to 4 carbon atoms, alkoxymethyl having up to 5 carbon atoms or alkoxy having 1 to 4 carbon atoms.

In the compounds of formula Ia, $R^{1a}$ may be tert.butyl, isopropyl, 1-hydroxypropyl-2 or 1-hydroxy-2-methyl-propyl-2, $R^{2a}$ may be methoxymethyl, 2-methoxyethyl, 3-methoxy-n-propyl, 4-methoxy-n-butyl, methoxymethoxy, 2-methoxyethoxy, 3-methoxy-n-propoxy, or 4-methoxy-n-butoxy and $R^{3a}$ may be chloro, bromo, methyl, allyl, methoxymethyl or methoxy.

One preferred group of amines are those according to formula Ib

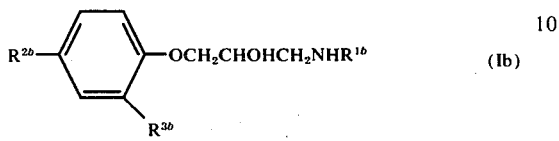

(Ib)

wherein $R^{1b}$ is alkyl having 1 to 4 carbon atoms, or alkyl having 1 to 4 carbon atoms, $R^{2b}$ is alkylthioalkyl having up to 8 carbon atoms, and $R^{3b}$ is halogen, alkyl having 1 to 4 carbon atoms, alkenyl having 2 to 4 carbon atoms, alkoxymethyl having up to 5 carbon atoms, and alkoxy having 1 to 4 carbon atoms.

In compounds of formula Ib, $R^{1b}$ may be tert.-butyl, or isopropyl, 1-hydroxy-propyl-2, or 1-hydroxy-2-methylpropyl-2, $R^{2b}$ may be methylthiomethyl, 2-methylthio-ethyl, 3-methylthio-n-propyl, or 4-methylthio-n-butyl and $R^{3b}$ may be chloro, bromo, methyl, allyl, methoxymethyl, methoxy or allyloxy. Preferably $R^{1b}$ is tert.-butyl, or isopropyl, $R^{2b}$ is 2-methylthio-ethyl or 3-methylthio-n-propyl and $R^{3b}$ is chloro, bromo, methyl, allyl, methoxymethyl, or methoxy.

Another preferred group of amines are those according to formula Ic

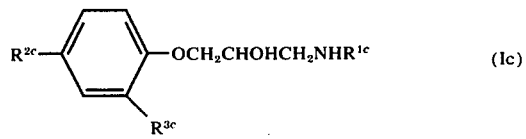

(Ic)

wherein $R^{1c}$ is alkyl having 1 to 4 carbon atoms, or hydroxyalkyl having 1 to 4 carbon atoms, $R^{2c}$ is alkoxycarbonylaminoalkyl having up to 9 carbon atoms, and $R^{3c}$ is halogen, alkyl having 1 to 4 carbon atoms, alkenyl having 2 to 4 carbon atoms, alkoxymethyl having up to 5 carbon atoms, or alkoxy having 1 to 4 carbon atoms.

In compounds of formula Ic, $R^{1c}$ may be tert.-butyl, isopropyl, 1-hydroxypropyl-2, or 1-hydroxy-2-methylpropyl-2, $R^{2c}$ may be methoxycarbonylaminomethyl, 2-methoxycarbonylaminoethyl, 3-methoxycarbonylamino-n-propyl or 4-methoxycarbonylamino-n-butyl and $R^{3c}$ may be chloro, bromo, methyl, allyl, methoxymethyl, methoxy or allyloxy. Preferably $R^{1c}$ is tert-butyl or isopropyl, $R^{2c}$ is 2-methoxycarbonylaminoethyl or 3-methoxycarbonylamino-n-propyl, and $R^{3c}$ is chloro, bromo, methyl, allyl, methoxymethyl, or methoxy.

The following compounds are especially mentioned:
1. 1-[2-bromo-4-(2-methoxyethyl)-phenoxy]-3-isopropylamino-propanol-2
2. 1-[2-chloro-4-(2-methoxyethyl)-phenoxy]-3-isopropylamino-propanol-2
3. 1-[2-chloro-4-(2-methoxyethyl)-phenoxy]-3-tert.-butylamino-propanol-2
4. 1-[2-bromo-4-(2-methoxyethoxy)-phenoxy]-3-isopropylamino-propanol-2,
5. 1-[2-methoxymethyl-4-(2-methoxyethyl)-phenoxy]-3-isopropylamino-propanol-2,
6. 1-[2-bromo-4-(2-methoxycarbonylaminoethyl)-phenoxy]-3-isopropylamino-propanol-2,
7. 1-[2-allyl-4-(2-methoxyethoxy)-phenoxy]-3-isopropylamino-propanol-2,
8. 1-[2-allyl-4-(3-methoxy-n-propyl)-phenoxy]-3-isopropylamino-propanol-2,
9. 1-[2-chloro-4-(3-methoxy-n-propyl)-phenoxy]-3-isopropylamino-propanol-2,
10. 1-[2-bromo-4-(3-methoxy-n-propyl)-phenoxy]-3-isopropylamino-propanol-2,
11. 1-[2-methoxy-4-(methoxymethyl)-phenoxy]-3-isopropylamino-propanol-2,
12. 1-[2-allyl-4-(2-methoxyethyl)-phenoxy]-3-isopropylamino-propanol-2,
13. 1-[2-n-propyl-4-(2-methoxyethyl)-phenoxy]-3-isopropylamino-propanol-2,
14. 1-[2-chloro-4-(2-methoxycarbonylaminoethyl)-phenoxy]-3-isopropylamino-propanol-2,
15. 1-[2-methoxy-4-(2-methoxycarbonylaminoethyl)-phenoxy]-3-isopropylamino-propanol-2,
16. 1-[2-fluoro-4-(2-methylmercaptoethyl)-phenoxy]-3-isopropylamino-propanol-2,
17. 1-[2-methoxy-4-(3-methoxy-n-propyl)-phenoxy]-3-isopropylamino-propanol-2,
18. 1-[2-fluoro-4-(2-methoxyethyl)-phenoxy]-3-isopropylamino-propanol-2 or
19. 1-[2-bromo-4-(methoxycarbonylaminomethyl)-phenoxy]-3-isopropylamino-propanol-2.

These compounds block the cardial β-receptors as is observed by the fact that they antagonize the tachycardia caused by intravenous injection of 0.5 μg/kg of d/l-isoprotorenol in an anaesthetized cat. A dose of 0.03 to 1 mg/kg is sufficient. Blockage of the vascular β-receptors is also shown by the fact that injection of 3 mg/kg of compounds of this invention will antagonize the vasodilation caused by intravenous injection of 0.5 μg/kg of isoprotorenol sulfate in an anaesthetized cat.

The compounds of this invention in a concentration of 0.03 to 1 μg/ml also have been shown in vitro to antagonize tachycardia caused by addition of 0.005 μg/ml of d/l-isoprotorenol sulfate to a bath containing an isolated guinea-pig heart.

The new compounds are obtained according to methods known per se. Thus, a compound of formula II

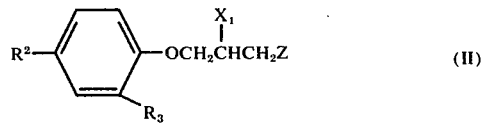

(II)

wherein $R^2$ and $R^3$ have the meanings given above, X is a hydroxy group and Z is a reactive, esterified hydroxy group or halogen or X and Z together form an epoxy group, is reacted with an amine of the formula $NH_2$—$R^1$, wherein $R^1$ has the same meaning as given above.

A reactive, esterified hydroxy group is obtained when a hydroxy group is esterified with a strong organic sulphonic acid as a strong aromathic sulphonic acid, e.g. benzenesulphonic acid, 4-bromobenzenesulphonic acid or 4-toluenesulphonic acid. Z being a halogen is obtained when the hydroxy group is reacted (or esterified) with a strong unorganic acid as hydrobromic acid, hydrochloric acid or hydroiodic acid, Z being bromine, chlorine or iodine.

Z is preferably halogen, e.g. bromine, chlorine or iodine as mentioned. Thus, Z is preferably chloro, bromo or iodo.

This reaction is carried out in a common way. At the use of a reactive ester as a starting material the preparation takes place preferably in the presence of a basic condensing agent and/or with an excess of an amine. Suitable basic condensing agents are e.g. alkalimetal hydroxides as sodium or potassium hydroxide, alkalimetal carbonates as potassium carbonate and alkalimetal alcoholates as sodium methylate, potassium ethylate and potassium tert.-butylate.

Further, a compound of formula III

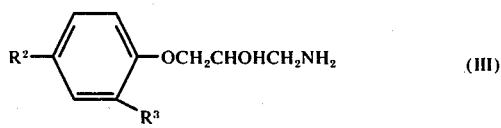

wherein $R^2$ and $R^3$ have the same meanings as given above, is reacted with a compound of the formula $Z—R^1$, wherein $R^1$ and Z have the same meanings as given above.

This reaction is carried out in a common way, preferably in the presence of a basic condensing agent and/or an excess of an amine. Suitable basic condensing agents are e.g. alkaline alcoholates, preferably sodium or potassium alcoholate, or also alkaline carbonates as sodium or potassium carbonate.

Further, a compound of formula IV

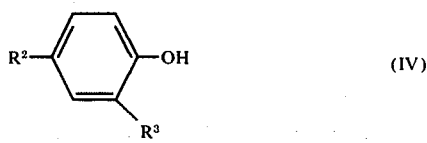

wherein $R^2$ and $R^3$ have the same meanings as given above is reacted with a compound of formula V

wherein Z, X and $R^1$ have the same meanings as given above.

This reaction is carried out in a common way. In those cases where reactive esters are used as starting material, the compound of formula IV may suitably be used in the form of its metalphenolate as alkalimetalphenolate, preferably sodiumphenolate, or one works in the presence of an acid binding agent, preferably a condensing agent, which can form a salt of the compound of formula IV as an alkalimetal alcoholate.

Further, one may split off a residue from a compound of formula I above, wherein $R^1$, $R^2$ and $R^3$ have the same meanings as above and in which the nitrogen atom of the amino group and/or the hydroxy group has attached thereto a splitable residue.

Such splitable residues are especially those which are splitable by solvolysis, reduction, pyrolysis or fermentation.

Residues splitable by solvolysis are preferably residues splitable by hydrolysis or ammonolysis.

Residues splitable by means of hydrolysis are e.g. an acyl residue, which, when present, are functionally varied carboxy groups, e.g. oxycarbonyl residues, as alkoxycarbonyl residues, e.g. tert.-butoxycarbonyl residue, or ethoxycarbonyl residue, aralkoxycarbonyl residues as phenylloweralkoxycarbonyl residues, e.g. a carbobensyloxy residue, halogencarbonyl residue, e.g. a chlorocarbonyl residue, further arylsulphonyl residues as toluenesulphonyl or bromobenzenesulphonyl residues, and possibly as halogenated, as fluorinated loweralkanoyl residues as formyl-, acetyl- or trifluoroacetyl residue or a bensyl residue or cyano groups or silyl residues, as trimethylsilyl residue.

Of the above mentioned residues present at the hydroxy groups, which residues are splitable by hydrolysis preferably, the oxycarbonyl residues and the loweralkanoyl residues or the benzoyl residues are used.

Besides the above mentioned also double-bonded residues, which are splitable at the amino group by hydrolysis are used, e.g. alkylidene or bensylidene residue or a phosphorylidene group as a triphenylphosphorylidene group, whereby the nitrogen atom then obtains a positive charge.

Residues splitable at the hydroxy group and the amino group by hydrolysis are furthermore divalent residues as in occurring cases substituted methylene. As substituents on the methylene residues any organic residue may be used, whereby it does not matter at the hydrolysis which compound is the substituent to the methylene residue. As methylene substituents e.g. aliphatic or aromatic residues as alkyl as mentioned above, aryl e.g. phenyl or pyridyl may be used. The hydrolysis may be carried out in any common way, suitably in a basic or preferably in an acid medium.

Compounds having residues being splitable by hydrolysis are also the compounds according to formula VI

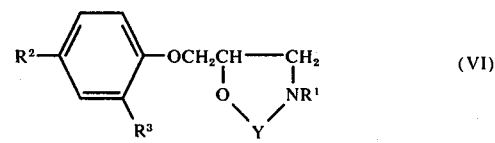

wherein $R^1$, $R^2$ and $R^3$ have the same meanings as given above and Y is a carbonyl or thiocarbonyl residue.

The hydrolysis is carried out in an analogous way, e.g. in the presence of a hydrolysing agent, e.g. in the presence of acidic agent as e.g. diluted mineral acids, as sulphuric acid or hydrohalogen acid, or in the presence of basic agents as e.g. alkalimetal hydroxides, as sodium hydroxide. Oxycarbonyl residues, aryl sulphonyl residues and cyano groups may in a suitable way be split off by means of acidic agents as by means of a hydrohalogen acid, suitably hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "bromocyano method" (v. Braun). Further, e.g. a tert.-butoxycarbonyl residue may be split off under anhydrous conditions by means of a treatment with a suitable acid, as trifluoroacetic acid. Acidic agents are preferably used at an hydrolysis of compounds of formula VI.

Residues splitable by ammonolysis are especially the halogen-carbonyl residues, as the chlorocarbonyl residue. The ammonolysis may be carried out in a common way, e.g. by means of an amine containing at least one hydrogen atom bounded to the nitrogen atom, as a mono- or diloweralkylamine, e.g. methylamine or dimethylamine, or especially ammonia, preferably at an elevated temperature. Instead of ammonia one may use an agent which gives ammonia as hexamethylenetetraamine.

Residues splitable by means of a reduction are e.g. an α-aryl-alkyl residue, as a benzyl residue or an α-aralkoxycarbonyl residue as a bensyloxycarbonyl residue, which in a common way may be split off be means of a hydrogenolysis, especially by catalytically activated hydrogen, as by hydrogen in the presence of hydrogenating catalysts, e.g. Raney-nickel. Further residues splitable by means of hydrogenolysis are 2-halogenalkoxycarbonyl residues as 2,2,2-trichloroethoxycarbonyl residues or 2-iodoethoxy- or 2,2,2-tribromoethoxycarbonyl residues, which may be split off in a common way, suitably by means of a metallic reduction (so called nascenting hydrogen). Nascenting hydrogen may be obtained by the influence of metal or metal alloys, as amalgam on compounds which give hydrogen as carboxyacids, alcohols or water, whereby especially zinc or zinc-alloys together with acetic acid may be used. Hydrogenolysis of 2-halogenalkoxycarbonyl residues may further take place using chromium or chromium (II) compounds as chromium (II) chloride or chromium (II) acetate.

A residue splitable by reduction may also be an arylsulphonyl group as a toluenesulphonyl group, which in a common way may be split off by reduction using nascerating hydrogen, e.g. by means of an alkalimetal, as lithium or sodium in liquid ammonia, and suitably may be split off from a nitrogen atom. At the carrying out of the reduction one has to take care of the fact that other reducing groups are not influenced.

Residues splitable by means of pyrolysis, especially residues splitable from the nitrogen atom, are in occurring cases substituted, suitably unsubstituted carbamoyl groups. Suitable substituents are e.g. loweralkyl or arylloweralkyl as methyl or benzyl or aryl, as phenyl. The pyrolysis is carried out in a common way, whereby one may have to take care of other thermically susceptible groups.

Residues splitable by means of fermentation, especially residues splitable from the nitrogen atom are in occurring cases substituted, however suitably unsubstituted carbamoyl groups. Suitable substituents are e.g. loweralkyl or arylloweralkyl, as methyl or benzyl, or aryl as phenyl. The fermentation is carried out in a common way, e.g. by means of enzyme urease or soy bean extract at about 20° C or a slightly elevated temperature.

Further, a Schiff's base of formula VII or VIII

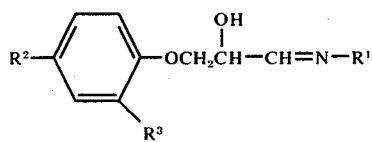

(VII)

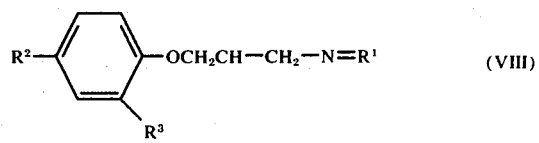

(VIII)

or a cyclic tautomer corresponding to formula VIII of formula IX

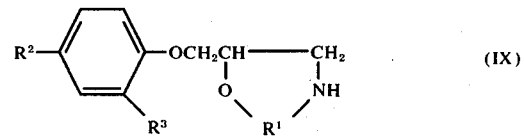

(IX)

can be reduced, wherein $R^1$, $R^2$ and $R^3$ have the same meaning as given above and $R^{1'}H$ is the same as $R^1$ and whereby the compounds of formula VIII and IX may exist together, too. This reduction is carried out in a common way, e.g. using a di-lightmetalhydride, as sodiumboronhydride, lithiumaluminiumhydride, using a hydride as Boran with formic acid, or by means of a catalytic hydrogenation, as with hydrogen in the presence of Raney-nickel. At the reduction one has to take care of the fact that other groups are not affected.

Further, the oxo group in the compound of formula X

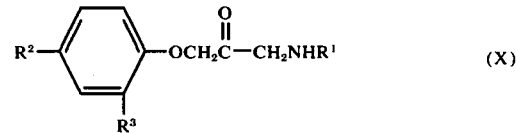

(X)

wherein $R^1$, $R^2$ and $R^3$ have the same meanings as given above, can be reduced to a hydroxy group. This reduction is carried out in a common way, especially using a di-lightmetalhydride, as mentioned above, or according to the "Neerwein-Pondorf-Verley method", or a modification thereof, suitably using an alkanol as a reaction component and as solvent, as isopropanol, and using a metalalkanolate, as metalisopropanolate, e.g. aluminium isopropanolate.

Further, in a compound of formula XI

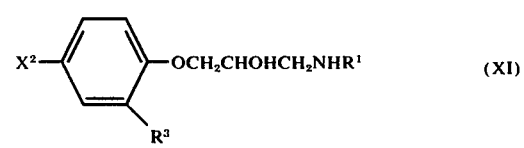

(XI)

wherein $R^1$ and $R^3$ have the same meanings as given above, and wherein $X^2$ is a residue which is able to be transformed to a residue $R^2$ having the same meaning as given above, one transforms $X^2$ to $R^2$.

A residue $X^2$ able to be transformed into $R^2$ is e.g. a residue $X^2$ transformable to a loweralkoxyloweralkyl or loweralkylthioloweralkyl residue $R^2$, as a $Z^1$-loweralkyl residue. A compound XI having such a residue $Z^1$-loweralkyl as $X^2$ can be reacted in a common way with a compound loweralkyl-$Z^2$, whereby one of $Z^1$ and $Z^2$ is a hydroxy group or mercapto group and the other being Z having the meaning given above. Thus, one can react either a compound of formula XII

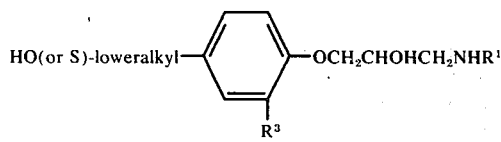

(XII)

with a compound loweralkyl-Z, or a compound of formula XIII

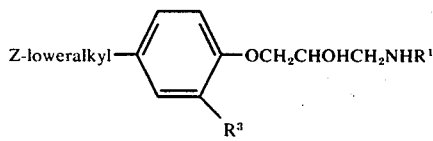

(XIII)

with a compound loweralkyl-O(S)H, whereby $R^1$, $R^3$ and Z have the same meanings as given above. The reaction is carried out in a common way, e.g. as the reaction of a compound of formula II with an amine $NH_2R^1$.

A residue $X^2$ transformable into $R^2$ is e.g. a residue $X^2$ transformable into a loweralkoxycarbonylaminoloweralkyl residue $R^2$, as a residue Z-loweralkyl. A compound XI with such a residue Z-loweralkyl as $X^2$ can be reacted in a common way with a loweralkoxycarbonylamino, whereby Z has the same meanings as given above. Thus, one can react a compound of the formula XIV

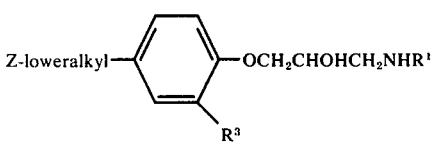

(XIV)

with a compound loweralkoxy-$CO-NH_2$, whereby $R^1$, $R^3$ and Z have the meanings given above. The reaction is carried out in a common way, e.g. as the reaction of a compound of formula II with an amine $NH_2-R^1$.

A residue $X^2$ transformable into $R^2$ is e.g. a residue $X^2$, transformable into a loweralkoxyloweralkoxy residue $R^2$ as a residue $Z^1$-loweralkyl-O- or a hydroxy group.

A compound XI having such a residue $Z^1$-loweralkyl-O- as $X^2$ can be reacted in a common way with a compound loweralkyl-$Z^2$, whereby one of the residues $Z^1$ and $Z^2$ is hydroxy and the other being Z having the same meaning as given above.

Thus, one can react a compound of formula XV

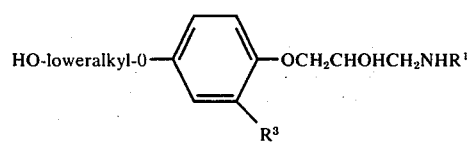

(XV)

with a compound loweralkyl-Z or a compound of formula XVI

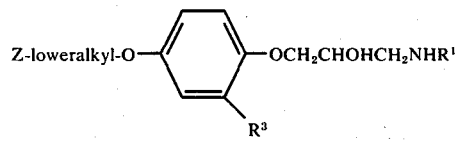

(XVI)

with a compound loweralkyl-OH, whereby $R^1$, $R^3$ and Z have the same meanings as given above. The reaction is carried out in a common way, e.g. as the reaction of a compound of formula II with an amine $NH_2-R^1$.

A compound of formula XI having a hydroxy group as a residue $X^2$ can be reacted in a common way with a compound loweralkoxyloweralkyl-Z, whereby Z has the same meaning as above.

Thus, one can react a compound of formula XVII (XVII)

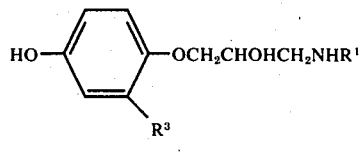

with a compound loweralkoxyloweralkyl-Z, wherein $R^1$, $R^3$ and Z have the same meanings as given above. The reaction is carried out in a common way, e.g. as the reaction of a compound of formula II with an amine $NH_2-R^1$.

Further, the oxo group in a compound corresponding to these of formula I and which carries an oxo group at a carbon atom bound to a nitrogen atom may be reduced to two hydrogen atoms. The residue R² is thereby preferably not a loweralkoxycarbonylamino-loweralkyl.

Said compounds are e.g. such of the formula XVIII

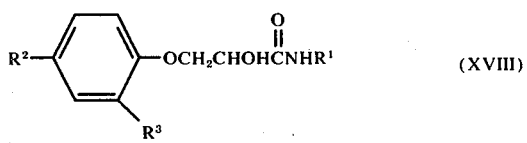

wherein R¹, R² and R³ have the meaning given above.

The reduction can be carried out according to the above described manner using complex metalhydrides, e.g.: lithiumaluminiumhydride or di-isobutylaluminiumhydride. Suitably the reaction takes place in an inert solvent as an ether, e.g. diethylether or tetrahydrofuran.

In a common way the substituents may be varied from the compounds obtained within the end product as well as the compounds obtained may be introduced, split off or transformed into other end-products in a common way.

Thus, it is possible to hydrogenate catalytically C-C double-bonds or C-C triplebonds to C-C single bonds by means of hydrogen in the presence of a hydrogenation catalyst, e.g. platinum, palladium or nickel, as Raney-nickel. Thereby one has to notice that other reducable groups are not reduced.

In compounds obtained containing a C—C triplebond this may further be transformed into a C—C doublebond and, if desired, be hydrogenated stereospecifically into a CC-C-cis or C-C-trans doublebond. The hydrogenation of a C—C triplebond to a C—C doublebond may for example be carried out using 1 mole of hydrogen in the presence of a less active hydrogenation catalyst as iron or palladium, e.g. Raney-iron or palladium with bariumsulphate, preferably at an elevated temperature. The hydrogenation to a C-C-cis doublebond may take place e.g. between 1 mole of hydrogen and a only partly aktive catalyst, as palladium on active carbon and in the presence of quinoline or palladium on calciumcarbonate in the presence of plumbum-II salts or Raney-nickel. The hydrogenation to a C-C-trans doublebond may take place by means of sodium in liquid ammonia, whereby with regard to other reducable groups short reaction times are used and no excess of the reducing agent is used, possibly an ammoniumhalogenide, as ammoniumchloride, being added as a catalyst.

At the reduction mentioned above one has to see to that no further reducable groups are reduced. At the reduction using Raney-nickel and hydrogen one has to consider especially a possibly present halogen atom bond to the aromathic ring, so that it is not replaced by hydrogen. Furthermore, at all reductions, especially catalytic hydrogenations, one has to consider any thioether group present. Preferably sulphur resistent catalysts are used and, in actual cases, the volume of hydrogen to be absorbed is calculated and when the calculated amount is absorbed at the hydrogenation the reduction is finished.

The above mentioned reactions may possibly be carried out simultaneously or after each other in any sequence.

The above mentioned reactions are carried out in a manner known per se in the presence or absence of diluting, condensating and/or catalytical agents at a low, room or an elevated temperature, possibly being carried out in a closed vessel.

Depending on the process conditions and the starting material the end product is obtained either in free form or in the form of its acid addition salt, which is included in the scope of the invention. Thus, for example, basic, neutral or mixed salts may be obtained as well as hemiamino, sesqui- or polyhydrates. The acid addition salts of the new compounds may in a manner known per se be transformed into free compounds using e.g. basic agents as alkali or ion exchanger. On the other hand, the free bases obtained may form salts with organic or inorganic acids. In the preparation of acid addition salts preferably such acids are used which form suitable therapeutically acceptable salts. Such acids are e.g. hydrohalogen acids, sulphuric acid, phosphoric acid, nitric acid, perchloric acid, aliphatic, alicyclic, aromathic or heterocyclic carboxy or sulphonic acids, as formic, acetic, propionic, succinic, glycolic, lactic, malic, tartaric, citric, ascorbic, maleic, hydroxymaleic or pyruvic acid, phenylacetic, benzoic, p-aminobenzoic, antranilic, p-hydroxybenzoic, salicylic or p-aminosalicylic acid, embonic acid, methanesulphonic, ethanesulphonic, hydroxyethanesulphonic, ethylenesulphonic acids, halogenbenzenesulphonic, toluenesulphonic, naphtylsulphonic acids or sulphanilic acid; methionine, tryptophane, lysine or arginine.

These or other salts of the new compounds as e.g. picrates may serve as purifying agents of the free bases obtained as the free bases are transformed into salts, these are separated and the bases are then set free from the salts again. According to the close relationship between the new compounds in free form and in the form of their salts it will be understood from the above and the below that, if possible, the corresponding salts are included in the free compounds.

The invention also relates to any embodiment of the process of which one starts from any compound obtained as an intermediate in any process step and one carries out the lacking process step, or one breaks off the process at any step, or at which one forms a starting material under the reaction conditions, or at which a reaction component possibly in the form of its salt is present.

Thus, one may react an aldehyde of the formula XIX

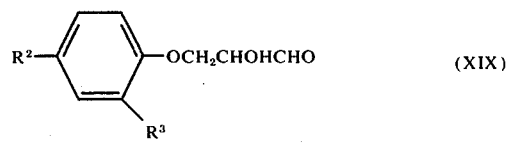

wherein R² and R³ have the same meaning as given above, with an amine of the formula H₂N—R¹, wherein R¹ has the same meanings as given above, in the presence of a suitable reducing agent, as one of the above mentioned. Thereby a compound of formula VII is obtained as an intermediate, which then is reduced according to the invention.

Further, one may in a manner known per se react an amine of the formula III with an aldehyde or a keton of the formula O=R1', wherein R1' has the above meaning in the presence of a suitable reducing agent, as one of the above mentioned. Thereby, a compound of formula VIII or IX is obtained as an intermediate, which then is reduced according to the invention.

The new compounds may, depending on the choice of starting materials and process, be present as optical antipodes or racemate, or, if they contain at least two asymmetric carbon atoms, be present as an isomer mixture (racemate mixture).

The isomer mixtures (racemate mixtures) obtained may, depending on physical-chemical differences of the components, be separated into the both stereoisomeric (diastereomeric) pure racemates, e.g. by means of chromatography and/or fractionated crystallisation.

The racemates obtained can be separated according to known methods, e.g. by means of recrystallisation from an optically active solvent, by means of microorganisms, or by a reaction with optically active acids forming salts of the compound and separating the salts thus obtained, e.g. by means of their different solubility in the diastereomeres, from which the antipodes by the influence of a suitable agent may be set free. Suitably useable optically active acids are e.g. the L- and D-forms of tartaric acid, di-o-tolyltartaric acid, malic acid, mandelic acid, camphersulphonic acid or china acid. Preferably the more active part of the two antipodes is isolated.

Suitably such starting materials are used for carrying out the reactions of the invention, which material leads to groups of end products primarily especially desired and especially to the specifically described and preferred end products.

The starting materials are known or may, if they should be new, be obtained according to processes known per se.

In clinical use the compounds of the invention are administered normally orally, rectally or by injection in the form of a pharmaceutical preparation, which contains an active component either as free base or as pharmaceutically acceptable, non-toxic acid addition salt, as e.g. the hydrochloride lactate, acetate, sulphamate or the like in combination with a pharmaceutically acceptable carrier. Thereby the mentioning of the new compounds of the invention is here related to either the free amine base or the acid addition salts of the free base, even if the compounds are generally or specifically described, provided that the context in whch such expressions are used, e.g. in the examples, with this broad meaning should not correspond. The carrier may be a solid, semisolid or liquid diluent or a capsule. These pharmaceutical preparations are a further object of the invention. Usually the amount of active compound is between 0.1 to 95 % by weight of the preparation, suitably between 0.5 to 20 % by weight in preparations for injection and between 2 to 50 % by weight in preparations for oral administration.

In the preparation of pharmaceutical preparations containing a compound of the present invention in the form of dosage units for oral administration the compound elected may be mixed with a solid, pulverulent carrier, as e.g. with lactose, saccharose, sorbitol, mannitol, starch, as potatoe starch, corn starch amylopectin, cellulose derivatives or gelatine, as well as with an antifriction agent as magnesium stearate, calcium stearate, polyethyleneglycol waxes or the like, and be pressed into tablets. If coated tablets are wanted, the above prepared core may be coated with concentrated solution of sugar, which solution may contain e.g. gum arabicum, gelatine, talc, titandioxide or the like. Furthermore, the tablets may be coated with a laquer dissolved in an easily volatile organic solvent or mixture of solvents. To this coating a dye may be added in order to easily distinguish between tablets with different active compounds or with different amounts of the active compound present.

In the preparation of soft gelatine capsules (pearl-shaped, closed capsules), which consist of gelatine and e.g. glycerine or in the preparation of similar closed capsules the active compound is mixed with a vegetable oil. Hard gelatine capsules may contain granules of the active compound in combination with a solid, pulverulent carrier as lactose, saccharose, sorbitol, mannitol, starch (as e.g. potatoe starch, corn starch or amylopectin), cellulose derivatives or gelatine.

Dosage units for rectal administration may be prepared in the form of suppositories, which contain the active substance in a mixture with a neutral fat base, or they may be prepared in the form of gelatine-rectal capsules which contain the active substance in a mixture with vegetable oil or paraffin oil.

Liquid preparations for oral administration may be present in the form of sirups or suspensions, e.g. solutions containing from about 0.2 % by weight to about 20 % by weight of the active substance described, whereby the residue consists of sugar and a mixture of ethanol, water, glycerol and propylene glycol. If desired, such liquid preparations may contain colouring agents, flavouring agents, saccharine and carboxymethylcellulose as a thickening agent.

Solutions for parenteral administration by injection may be prepared as an aqueous solution of a watersoluble pharmaceutically acceptable salt of the active compound, preferably in a concentration from about 0.5 % by weight to about 0.10 % by weight. These solutions may also contain stabilizing agents and/or buffering agents and may suitably be available in different dosage unit ampoules.

The preparation of pharmaceutically tablets for peroral use is carried out in accordance with the following method:

The solid substances included are ground or sieved. The binding agent is homogenized and suspended in solvent. The therapeutic compound and necessary auxiliary agents are mixed during a continuous and constantly mixing with the binding agent solution and are moistened so that the solution is uniformly divided in the mass without overmoistening any parts. The amount of solvent is so adapted that the mass obtains a consistency reminding of wet snow. The moistening of the pulverulent mixture with the binding agent solution causes the particles to gather together slightly to aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and is standardized as the damp degree of the granulate is of important for the following process and for the feature of the tablets. Drying in a fluid bed may be used. In this case the mass is not put on a tray but is poured into a container having a net bottom.

After the drying step the granules are sieved. Under certain circumstances powder has to be removed.

To the so called final mixture, disintegrating, lubricants and antiadhesive agents are added. After this mixture the mass has its right composition for the tabletting step.

The cleaned tablet punching machine is provided with a set of punches and dies, whereupon the weight of the tablets and the degree of compression is set. The weight of the tablet is decisive for the size of the dose in each tablet and is calculated starting from the amount of therapeutic agent in the granules. The degree of compression affects the size of the tablet, its strength and its ability of disintegrate in water. Especially as regards the two later properties the choice of compression pressure (0.5 to 5 ton) is a balance-step. When the right adjustment is set, the preparation of tablets is started, which is carried out with a rate of 20,000 to 200,000 tablets per hour. The pressing of the tablets requires different times and depends on the size of the batch.

The tablets are freed from adhering pulver in a specific apparatus and are then stored in closed packages until they are delivered.

Many tablets, especially these which are rough or bitter, are coated with a coating. This means that they are coated with a layer of sugar or some other suitable coating.

The tablets are usually packed by machines having an electronic counting device. The different types of packages consist of glass or plastic gallipots, but also boxes, tubes and specific dosage adapted packages.

The daily dose of the active substance varies and is depending on the type of administration, but as a general rule it is 100 to 400 mg/day of active substance at peroral administraion and 5 to 20 mg per day at intravenous administration.

The following illustrates the principle and the adaptation of the invention, however, without being limited thereto. Temperature is given in degree Centigrade.

EXAMPLE 1

1,2-Epoxy-3-[2'-bromo-4'-(β-methoxyethyl)-phenoxy]-propane (20.5 g) was mixed with 25 ml of isopropanol and 25 ml of isopropylamine. The mixture is then heated on a boiling water-bath for 3 hours under reflux. Thereupon the reaction mixture is evaporated to dryness and the residue is dissolved in ether and the hydrochloride precipitates on the addition of gaseous HCl in either at pH 4–5. After recrystallisation from methylethylketon the hydrochloride of 1-isopropylamino-3-[2'-bromo-4'-(β-methoxyethyl)-phenoxy]-propanol-2 is obtained. Melting point 140° C. Equ. weight: found: 383, calculated: 383.

In accordance with the method of example 1 the following compounds are obtained as hydrochlorides.

EXAMPLE 2

1-Isopropylamino-3-[2'-chloro-4'-(2-methoxyethyl)-phenoxy]-propanol-2. Melting point 140° C. Equ. weight: found: 338, calculated: 338.

EXAMPLE 3

1-tert.-butylamino-3-[2'-chloro-4'-(2-methoxyethyl)-phenoxy]-propanol-2. Melting point 106° C. Equ. weight: found: 353, calculated: 352. Tert.-butylamine has been used instead of isopropylamine of Example 1.

EXAMPLE 4

1-Isopropylamino-3-[2'-bromo-4'-(2-methoxyethoxy)-phenoxy]-propanol-2. Melting point 127° C. Equ. weight: found: 403, calculated: 399.

EXAMPLE 5

1-Isopropylamino-3-[2'-methoxymethyl-4'-(2-methoxyethyl)-phenoxy]-propanol-2.

EXAMPLE 6

1-Isopropylamino-3-[2'-bromo-4'-(2-methoxycarbonylaminoethyl)-phenoxy]-propanol-2. Melting point 114° C. Equ. weight: found: 429, calculated: 426.

EXAMPLE 7

1-Isopropylamino-3-[2'-allyl-4'-(2-methoxyethoxy)-phenoxy]-propanol-2. Melting point 95° C. Equ. weight: found: 356, calculated: 360.

EXAMPLE 8

1-Isopropylamino-3-[2'-chloro-4'-(3-methoxy-n-propyl)-phenoxy]-propanol-2. Melting point 120° C. Equ. weight: found: 353, calculated: 352.

EXAMPLE 9

1-Isopropylamino-3-[2'-bromo-4'-(3-methoxy-propyl)-phenoxy]-propanol-2. Melting point 130° C. Equ.weight: found: 400, calculated: 397.

EXAMPLE 10

1-Isopropylamino-3-[2'-methoxy-4'-methoxymethyl-phenoxy]-propanol-2. Melting point 112° C. Equ.-weight: found: 313, calculated: 320.

EXAMPLE 11

1-Isopropylamino-3-[2'-allyl-4'-(2-methoxyethyl)-phenoxy]-propanol-2. Melting point 86° C. Equ.-weight: found: 346, calculated: 334.

EXAMPLE 12

1-Isopropylamino-3-[2'-propyl-4'-(2-methoxyethyl)-phenoxy]-propanol-2. Melting point 90° C. Equ.-weight: found: 347, calculated: 346.

In accordance with the method of Example 1 without any addition of HCl the following compounds were obtained as bases.

EXAMPLE 13

1-Isopropylamino-3-[2'-chloro-4'-(2-methoxycarbonylaminoethyl)-phenoxy]-propanol-2. Melting point 96° C. Equ.weight: found: 342, calculated: 344.

EXAMPLE 14

1-Isopropylamino-3-[2'-methoxy-4'-(2-methoxycarbonylaminoethyl-phenoxy]-propanol-2. Melting point 89° C. Equ.weight: found: 344, calculated: 340.

EXAMPLE 15

1-Isopropylamino-3-[2'-allyl-4'-(3-methoxy-n-propyl)-phenoxy]-propanol-2. Melting point: oil. Equ.-weight: found: 331, calculated: 321.

EXAMPLE 16

1-Isopropylamino-3-[2'-fluoro-4'-(2-methylmercaptoethyl)-phenoxy]-propanol-2xHCl. Melting point 99° C. Equ.weight: found: 338, calculated: 338.

EXAMPLE 17

1-Isopropylamino-3-[2'-methoxy-4'-(3-methoxy-n-propyl)-phenoxy]-propanol-2xHCl. Melting point 90° C. Equ.weight: found: 327, calculated: 322.

EXAMPLE 18

1-Isopropylamino-3-[2'-fluoro-4'-(2-methoxyethyl)-phenoxy]-propanol-2xHCl. Melting point 80° C. Equ.-weight: found: 346, calculated: 348.

EXAMPLE 19

1-Isopropylamino-3-[2'-bromo-4'-(methoxycarbonylaminomethyl)-phenoxy]-propanol-2xHCl. Melting point 175° C. Equ.weight: found: 415, calculated: 412.

EXAMPLE 20 (Method A)

To 18.7 g of 2-chloro-4-($\beta$-methoxyethyl)-phenol 200 ml of epichlorohydrine and 0.5 ml of piperidine were added, wehreupon the mixture was heated on a boiling waterbath during 10 hours. Thereupon the solvent was evaporated in vacuo and the residue was dissolved in chloroform and was extracted with 2 N HCl. The chloroform phase was shaken with $H_2O$ and evaporated. The residue was dissolved in 50 ml of isopropanol, to which mixture 50 ml of isopropylamine was added and the resulting mixture was refluxed for 10 hours. The solvent was evaporated and to the residue 2 N NaOH was added, whereupon it was extracted with ether, the ether phase being dried and evaporated. The residue was transformed into its hydrochloride in accordance with Example 1, which hydrochloride was recrystallized from methylethyl-keton. 1-Isopropylamino-3-[2'-chloro-4'-(2-methoxyethyl)-phenoxy]-propanol-2xHCl mp 140° C was obtained. Equ.weight: found: 339, calculated: 338.

EXAMPLE 21 (Method B)

A solution of 2-chloro-4-($\beta$-methoxyethyl)-phenylglycidyl ether (10 g) in 100 ml of ethanol was saturated with gaseous ammonia and the mixture was then heated in an autoclave on a boiling water-bath during 4 hours. Thereupon the solvent was evaporated, the residue was dissolved in ethyl acetate and HCl gas was introduced therein. Thereby the hydrochloride precpitated, which was filtered off and dissolved in 60 ml of ethanol. To the solution 20 ml of isopropyliodide and 15 g of potassium carbonate were added. The mixture was heated in an autoclave at 120° C during 10 hours, whereupon the ethanol was evaporated and the residue was dissolved in 100 ml of 2 N HCl and 100 ml of ether. The aqueous phase was separated and made alkaline with 2 N NaOH and extracted with ethyl acetate. The ethyl acetate phase was dried over potassium bicarbonate, whereupon the hydrochloride was precipitated with gaseous HCl. In this way the hydrochloride of 1-Isopropylamino-3-[2'-chloro-4'-(2-methoxyethyl)-phenoxy]-propanol-2 was obtained. Mp 141° C. Equ.-weight: found: 338, calculated: 338.

EXAMPLE 22 (Method C)

1.2 g of sodium was dissolved in 50 ml of ethanol and to the solution 12.4 g of 2-bromo-4-(2-methoxyethoxy) phenol and 7.6 g of 1-isopropylamino-3-chloropropanol-2were added, whereupon the mixture was heated in an autoclave on a boiling water-bath over night. Thereupon it was filtered and the filtrate was evaporated to dryness. To the residue 2 N HCl was added and the resulting mixture was extracted with ether. The aqueous phase was made alkaline using 2 N NaOH and extracted with ether. The ether phase was dried over potassium carbonate, whereupon the hydrochloride was precipitated with gaseous HCl. Thereby the hydrochloride of 1-isopropylamino-3-[2'-bromo-4'-(2-methoxyethoxy)-phenoxy]-propanol-2 was obtained. Recrystallized from ethylacetate the m.p. was 127° C. Equ.weight: found: 401, calculated: 399.

EXAMPLE 23 (Method D)

The aforegoing experiment was repeated but instead of 1-isopropylamino-3-chloropropanol-2 an equivalent amount of N-benzyl-1-isopropylamino-3-chloropropanol-2 was used. Thereby the hydrochloride of N-benzyl-1-isopropylamino-3-[2'-bromo-4'-(2-methoxyethoxy)-phenoxy]-propanol-2was obtained, which was dissolved in ethanol, to which a Pd/C catalyst had been added, and was hydrogenated to the calculated amount of hydrogen had been absorbed. After filtration the filtrate was evaporated to dryness and the residue was recrystallized from ethylacetate. The melting point obtained was 128° C. Equ.weight: found: 398, calculated: 399.

EXAMPLE 24 (Method E)

In accordance with the description of method B above 1-amino-3-[2'-chloro-4'-(2-methoxyethyl)-phenoxy]-propanol-2 was prepared. 5 g of this compound were dissolved in 50 ml of methanol and 10 ml of acetone. The solution was chilled to 0° C and at this temperature 5 g of sodiumboronhydride were added little by little. The temperature was then allowed to raise to room temperature and after 1 hour 150 ml of $H_2O$ and the solution was extracted with ether. The ether phase was dried over potassiumcarbonate and evaporated. The residue was transformed into its hydrochloride. In this way 1-isopropylamino-3-[2'-chloro-4'-(2-methoxyethyl)-phenoxy]-propanol-2 was obtained having the m.p. 140° C. Equ.weight: found: 340, calculated: 338.

EXAMPLE 25 (Method H)

18.7 g of 2-chloro-4-(2-methoxyethyl)-phenol were dissolved in a solution of 4.6 g of sodium in 100 ml of ethanol. To the solution 12.5 g of 2-hydroxy-3-chloropropionic acid was added and the resulting mixture was refluxed during 3 hours. Thereupon the solvent was evaporated and to the residue 100 ml of 2 N HCl were added. This was extracted with benzene. The benzene phase was shaken with a sodiumbicarbonate solution, which then was made acid using HCl. The aqueous phase was then extracted with benzene and after evaporation 2-hydroxy-3-[2'-chloro-4'-(2-methoxyethyl)-phenoxy]-propionic acid was obtained, from which the N-isopropylamide was prepared by dissolving the acid in tetra hydrofuran, adding isopropylamine, and dicyclohexyldicabodi-imide, and heating at 40° C for 5 hours. After filtration 5 g of lithiumaluminiumhydride were added to the filtrate and this was refluxed over night while stirring. After a preparation in accordance with known methods and a transfer to the hydrochloride the hydrochloride of 1-isopropylamino-3-[2'-chloro-4'-(2-methoxyethyl)-phenoxy]-propanol-2 having a m.p. of 140° C was obtained. Equ.weight: found: 337, calculated: 338.

EXAMPLE 26

A syrup containing 2 % (weight per volume) of active substance was prepared from the following ingredients:

| | |
|---|---|
| 1-Isopropylamino-3-[2'-bromo-4'-(methoxyethyl)-phenoxy]-propanol-2 . HCl | 2.0 g |
| Saccharine | 0.6 g |
| Sugar | 30.0 g |
| Glycerine | 5.0 g |
| Flavouring agent | 0.1 g |
| Ethanol 96 % | 10.0 ml |
| Distilled water | ad 100.0 ml |

Sugar, saccharine and the ethersalt were dissolved in 60 g of warm water. After cooling glycerine and a solution of flavouring agents dissolved in ethanol were added. To the mixture water was then added to 100 ml.

The above given active substance may be replaced with other pharmaceutically acceptable acid addition salts.

EXAMPLE 27

1-Isopropylamino-3-[2'-chloro-4'-($\beta$-methoxyethyl)-phenoxy]-propanol-2-hydrochloride (250 g) was mixed with lactose (175.8 g.), potatoe starch (169.7 g) and colloidal silicic acid (32 g). The mixture was moistened with a 10 % solution of gelatine and was granulated through a 12-mesh sieve. After drying potatoe starch (160 g), talc (50 g) and magnesium stearate (5 g) were admixed and the mixture thus obtained was pressed into tablets (10.000) which contain 25 mg of substance. The tablets are sold on the market provided with a breaking score to give another dose than 25 mg or to give multiples thereof when broken.

EXAMPLE 28

Granules were prepared from 1-isopropylamino-3-[2'-allyl-4'-($\beta$-methoxyethoxy)-phenoxy]-propanol-2-hydrochloride (250 g), lactose (175.9 g) and an alcoholic solution of polyvinylpyrrolidone (25 g). After the drying step the granules were mixed with talc (25 g), potatoe starch (40 g) and magnesium stearate (2.50 g) and was pressed into 10.000 tablets being biconvex. These tablets are primarily coated with a 10 % alcoholic solution of schellac and thereupon with an aqueous solution containing saccharose (45 %), gum arabicum (5 %), gelatine (4 %) and dyestuff (0.2 %). Talc and powder sugar were used for powdering after the first five coatings. The coating was then coated with a 66 % sugar sirup and polished with a 10 % carnauba wax solution in carbon tetrachloride.

EXAMPLE 29

1-Isopropylamino-3-[2'-bromo-4'-($\beta$-methoxycarbonylaminoethyl)-phenoxy]-propanol-2-hydrochloride (1 g), sodiumchloride (0.8 g) and ascorbic acid (0.1 g) were dissolved in sufficient amount of distilled water to give 100 ml of solution. This solution, which contains 10 mg of active substance on each ml, was used in filling ampoules, which were sterilized by heating at 120° C for 20 minutes.

PHARMACOLOGICAL EVALUATION

Compounds prepared according to the examples were evaluated for intrinsic activity and blocking effect on heart rate and peripheral vasodilator response to isoprenaline in the cat. Alprenolol was used as a reference substance.

Cats weighing between 1.8 and 2.8 kg were anaesthetized with 39 mg/kg pentobarbital sodium, intraperitoneally. The cats had been pretreated with reserpine, 5 mg/kg intramuscular, about 18 hours before the experiment. Bilateral vagotomy was performed before the start of the experiment.

The heart rate was recorded on an Offner cardiotachometer triggered by the EKG-complex. Mean arterial blood pressure was recorded from a carotid artery. The peripheral resistance was measured in one of the legs of the cat in the following way: The femoral artery was opened in the inguinal region and the leg was perfused by blood delivered through a sigma motor pump at constant rate. The flow resistance (the pressure) was recorded via a pressure transducer connected to the catheter distally to the pump. The paw was excluded from the circulation by a tight ligature intravenously injected isoprenaline increased the heart rate and reduced the perfusion pressure. An isoprenaline dose giving 70–80 % of the maximal chornotropic response was determined. This dose (usually 0.1 $\mu$g/kg) was then repeated with 20 minute intervals. Ten minutes before each isoprenaline injection, the tested substances were administered intravenously for 2 minutes, starting with a dose of 0.01 mg/kg and increasing each subsequent dose fourfold. The intrinsic effects of the test substances were determined. The dose producing 50 % blockade of the isoprenaline responses were evaluated from the plotted log dose-per cent blockade diagrams.

Table I shows the results of the foregoing experiments for intrinsic stimulating activity on heart rate in cats, $\beta$-blocking activity on heart rate and peripheral vascular resistance in cats and $LD_{50}$ after intraperitoneal administration in mice of compounds of the formula I

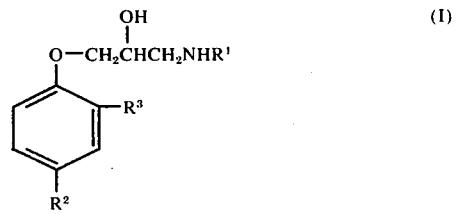

(I)

Reference is made ot the aforegoing examples only in order to simplify the Table I.

0-allyl (alprenolol) means 1-isopropylamino-3-(2-allylphenoxy)-propanol-2.

TABLE I

| Compounds Tested | Reserpinized cat | | |
|---|---|---|---|
| (Figures relate to the above examples and compounds prepared therein o-allyl(alprenolol) | Intrinsic activity % of maximal isoprenaline heart rate 20 | $\beta$-blockade Heart rate $ED_{50}$mg/kg 0.1 | $\beta$-blockade peripheral vascular resistance $ED_{50}$ mg/kg 0.005 |
| 1 | 0 | 0.03 | 1 |
| 2 | 0 | 0.1 | 3 |
| 3 | 0 | 0.03 | 1 |
| 4 | 22 | 0.06 | 9 |
| 5 | 5 | 0.2 | 5 |
| 6 | 0 | 0.3 | 3 |
| 7 | 34 | 0.05 | 3.8 |
| 8 | 0 | 0.3 | 2 |
| 9 | 0 | 0.4 | 1.5 |
| 10 | 1 | 0.6 | 3 |
| 11 | 0 | 0.1 | 0.8 |

TABLE I-continued

| Compounds Tested | Reserpinized cat | | |
|---|---|---|---|
| (Figures relate to the above examples and compounds prepared therein o-allyl(alprenolol) | Intrinsic activity % of maximal isoprenaline heart rate 20 | β-blockade Heart rate ED₅₀mg/kg 0.1 | β-blockade peripheral vascular resistance ED₅₀ mg/kg 0.005 |
| 12 | 0 | 0.1 | 0.5 |
| 13 | 0 | 0.1 | 3.5 |
| 14 | 0 | 0.3 | 3 |
| 15 | 0 | 0.3 | 1 |
| 16 | 0 | 0.2 | 1 |
| 17 | 0 | 0.4 | 5 |
| 18 | 0 | 0.05 | 2.7 |
| 19 | 0 | 0.1 | 1 |

The results reported in Table I, show that the phenoxy-hydroxypropylamine test substances according to the invention were up to 6 times less active than alprenolol, but also more active than alprenolol the standard reference, as regards blockade of the β-receptors of the heart. The peripheral vascular β-blocking activity for the test substances was 20–180 times lower than the activity of alprenolol. These results demonstrate that the test substances, developed a relatively stronger blockade of the β-receptors of the heart than of the receptors in smooth muscles. Due to this cardioselectivity, the compounds according to the invention give therapeutic effects in treating cardiovascular diseases without risk or complications due to β-blockade in bronchi and blood vessels.

We claim:

1. A compound according to the formula

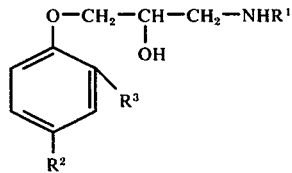

or a pharmaceutically acceptable non-toxic acid addition salt thereof,
wherein $R^1$ is an alkyl or hydroxyalkyl radical of 1 to 4 carbon atoms; $R^2$ is alkoxyalkoxy of 1 to 4 carbon atoms in each alkyl part, wherein the alkyl parts may be the same or different; and $R^3$ is selected from the group consisting of hydrogen, alkyl of 1 to 4 carbon atoms, alkenyl and alkinyl of 2 to 4 carbon atoms, alkoxymethyl of 2 to 4 carbon atoms; and alkoxy of 1 to 4 carbon atoms.

2. A compound according to claim 1 wherein $R^1$ is an alkyl group of 1 to 4 carbon atoms; $R^2$ is methoxyethoxy; and $R^3$ is selected from the group consisting of halogen, alkyl of 2 to 4 carbon atoms, alkenyl of 1 to 4 carbon atoms, alkoxymethyl of 2 to 4 carbon atoms and alkoxy of 1 to 4 carbon atoms.

3. The compound according to claim 1 which is 1-[2-bromo-4-(2-methoxyethoxy)-phenoxy]-3-isopropylamino propanol-2.

4. The compound according to claim 1 which is 1-[2-allyl-4-(2-methoxyethoxy)-phenoxy]-3-isopropylamino propanol.

5. A pharmaceutical composition providing cardioselective antagonism to adrenergic β-receptor stimulation containing as an active ingredient, in dosage units effective to provide said cardioselective antagonism to adrenergic β-receptor stimulation, an ortho-para-substituted phenoxy-hydroxypropylamine compound of the formula

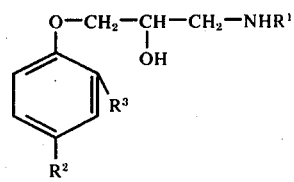

or a pharmaceutically acceptable non-toxic acid addition salt thereof,
wherein $R^1$ is an alkyl or hydroxyalkyl radical of 1 to 4 carbon atoms; $R^2$ is alkoxyalkoxy of 1 to 4 carbon atoms in each alkyl part, wherein the alkyl parts may be the same or different; and $R^3$ is selected from the group consisting of halogen, alkyl of 1 to 4 carbon atoms, alkenyl and alkinyl of 2 to 4 carbon atoms, alkoxymethyl of 2 to 4 carbon atoms, and alkoxy of 1 to 4 carbon atoms,
together with a pharmaceutically acceptable carrier.

6. A pharmaceutical preparation according to claim 5 wherein the active ingredient is 1-[2-bromo-4-(2-methoxyethoxy)-phenoxy]-3-isopropylaminopropanol-2 or a pharmaceutically acceptable non-toxic addition salt thereof.

7. A pharmaceutical preparation according to claim 5 wherein the active ingredient is 1-[2-allyl-4-(2-methoxyethoxy)-phenoxy]-3-isopropylaminopropanol-2 or a pharmaceutically acceptable non-toxic addition salt thereof.

8. A pharmaceutical composition providing cardioselective antagonism to adrenergic β-receptor stimulation containing as an active ingredient, in dosage units effective to provide said cardioselective antagonism to adrenergic β-receptor stimulation, an ortho-para-substituted phenoxy-hydroxypropylamine compound of the formula

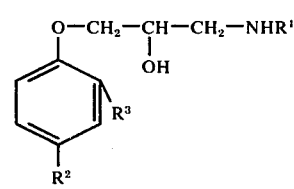

or a pharmaceutically acceptable non-toxic acid addition salt thereof,
wherein $R^1$ is an alkyl group of up to 4 carbon atoms, $R^2$ is methoxyethoxy and $R^3$ is selected from the group consisting of halogen, alkyl of 1 to 4 carbon atoms, alkenyl of 2 to 4 carbon atoms, alkoxymethyl of 2 to 4 carbon atoms, and alkoxy of 1 to 4 carbon atoms,
together with a pharmaceutically acceptable carrier.

9. A method providing for cardioselective antagonism to adrenergic β-receptor stimulation in an animal which comprises administering an amount effective to provide said cardioselective antagonism to adrenergic β-receptor stimulation of an ortho-para-substituted phenoxy-hydroxypropylamine compound of the formula

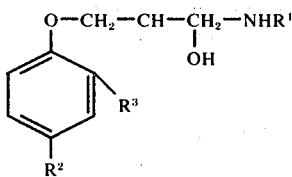

or a pharmaceutically acceptable non-toxic acid addition salt thereof,
wherein $R^1$ is an alkyl or hydroxyalkyl radical of 1 to 4 carbon atoms; $R^2$ is alkoxyalkoxy of 1 to 4 carbon atoms in each alkyl part, wherein the alkyl parts may be the same or different; and $R^3$ is selected from the group consisting of halogen, alkyl of 1 to 4 carbon atoms, alkenyl and alkinyl of 2 to 4 carbon atoms, alkoxymethyl of 2 to 4 carbonatoms, and alkoxy of 1 to 4 carbon atoms.

10. A method according to claim 9 wherein the phenoxyhydroxypropylamine compound is 1-[2-bromo-4-(2-methoxyethoxy)-phenoxy]-3-isopropylaminopropanol-2.

11. A method according to claim 9 wherein the phenoxyhydroxypropylamine compound is 1-[2-allyl-4-(2-methoxyethoxy)-phenoxy]-3-isopropylaminopropanol-2.

12. A method providing for cardioselective antagonism to adrenergic β-receptor stimulation in an animal which comprises administering an amount effective to provide said cardioselective antagonism to adrenergic β-receptor stimulation of an ortho-para-substituted phenoxy-hydroxypropylamine compound of the formula

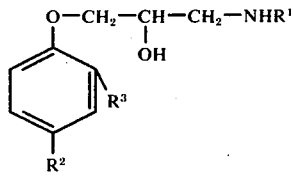

or a pharmaceutically acceptable non-toxic acid addition salt thereof,
wherein $R^1$ is an alkyl group of up to 4 carbon atoms, $R^2$ is methoxyethoxy and $R^3$ is selected from the group consisting of halogen, alkyl of 1 to 4 carbon atoms, alkenyl of 2 to 4 carbon atoms, alkoxymethyl of 2 to 4 carbon atoms and alkoxy of up to 4 carbon atoms.

* * * * *

UNITED STATES PATENT AND TRADEMARK OFFICE
CERTIFICATE OF CORRECTION

PATENT NO. : 3,996,382
DATED : December 7, 1976
INVENTOR(S) : Berntsson et al.

It is certified that error appears in the above-identified patent and that said Letters Patent are hereby corrected as shown below:

[75] Inventors: "Sven Erik Sjastrand" should be -- Sven Erik Sjostrand --;
Col. 8, "$R^1$" in formulas VIII & IX should read -- $R^{1'}$ --;
Col. 11, line 33, "CC-C-cis" should be -- C-C-cis --;
Col. 15, line 50, "either" should be -- ether --;
Col. 17, line 21, "wehreupon" should be -- whereupon --;
Col. 18, line 60, Signed and Sealed this Thirty-first Day of May 1977

[SEAL]

Attest:

RUTH C. MASON
Attesting Officer

C. MARSHALL DANN
Commissioner of Patents and Trademarks